(12) United States Patent
Jin et al.

(10) Patent No.: US 8,671,772 B2
(45) Date of Patent: Mar. 18, 2014

(54) QUALITY ASSURANCE AND RELIABILITY TESTING APPARATUS FOR RFID TAGS

(75) Inventors: Sung Ryol Jin, Milpitas, CA (US); Yong Hyun Lee, Milpitas, CA (US)

(73) Assignee: Hana Micron America, Inc., Milpitas, CA (US)

( * ) Notice: Subject to any disclaimer, the term of this patent is extended or adjusted under 35 U.S.C. 154(b) by 238 days.

(21) Appl. No.: 13/241,132

(22) Filed: Sep. 22, 2011

(65) Prior Publication Data

US 2013/0074607 A1    Mar. 28, 2013

(51) Int. Cl.
*G01N 3/20*    (2006.01)

(52) U.S. Cl.
USPC .......................................................... 73/849

(58) Field of Classification Search
USPC .................................... 73/760, 849, 855–856
See application file for complete search history.

(56) References Cited

U.S. PATENT DOCUMENTS

| | | | |
|---|---|---|---|
| 7,516,644 B2 * | 4/2009 | Wong et al. ................... | 73/12.07 |
| 7,746,234 B2 * | 6/2010 | Baba et al. .................. | 340/572.8 |
| 7,786,873 B2 * | 8/2010 | Baba et al. .................. | 340/572.7 |
| 7,902,983 B2 * | 3/2011 | Kobayashi et al. ........ | 340/572.1 |
| 7,954,228 B2 * | 6/2011 | Kobayashi et al. ............. | 29/600 |
| 7,960,215 B2 * | 6/2011 | Kobayashi et al. ........... | 438/126 |
| 7,982,295 B2 * | 7/2011 | Kobayashi et al. ........... | 257/679 |

* cited by examiner

*Primary Examiner* — Max Noori
(74) *Attorney, Agent, or Firm* — Samuel S. Cho; Invent Capture, LLC.

(57) ABSTRACT

A novel RFID tag-bending test apparatus and a related method of using the novel RFID tag-bending test apparatus are disclosed. In one embodiment of the invention, the novel RFID tag-bending test apparatus can place a plurality of RFID tags in corresponding tag holding clips on the novel RFID tag-bending test apparatus to execute a bending test sequence along a particular bending axis for each RFID tag. The bending test sequence can assist identifying defective RFID tags which cannot overcome external bending pressures asserted by the novel RFID tag-bending test apparatus. By excluding these defective RFID tags from a commercial shipment of RFID tags to customers, a manufacturer of RFID tags may be able to reduce a rate of premature RFID tag failures due to external bending pressures in real-life applications of RFID tags, thereby achieving a higher quality assurance and reliability of RFID tags.

13 Claims, 9 Drawing Sheets

| Front/Back | Direction | Defective Tag | Defective Rate |
|---|---|---|---|
| front | horizontal | 1 | 1.0% |
| | vertical | 28 | 28.0% |
| | diagonal (/) | 24 | 24.0% |
| | diagonal (\) | 22 | 22.0% |
| back | horizontal | 0 | 0.0% |
| | vertical | 1 | 1.0% |
| | diagonal (/) | 3 | 3.0% |
| | diagonal (\) | 2 | 2.0% |

400

QUALITY ASSURANCE AND RELIABILITY TESTING APPARATUS FOR RFID TAGS

BACKGROUND OF THE INVENTION

The present invention generally relates to quality assurance and reliability testing of wireless information devices. More specifically, various embodiments of the present invention relate to one or more apparatuses for quality assurance and reliability testing of RFID tags after the RFID tags are manufactured.

Radio-frequency identification (RFID) tags are increasingly becoming popular forms of identification for livestock, agricultural produce, and other food sources and products. In case of livestock farms, a conventional form of identifying an animal in a livestock herd is attaching a paper tag with an identification number on the animal's body part. If the paper tag is to be associated with the animal's vaccination history or any other pertinent dynamically-changing information, it is common practice to attach little paper tabs containing snippets of information to the paper tag itself, which make livestock farm management cumbersome, outdated, and awkward for any computerized information management of animal-specific and/or farm-specific data.

Using RFID tags to store animal-specific and farm-specific information enables electronic data storage and retrieval using an RFID reader device. Food source information tracking, contamination/disease breakout control, and/or transaction history tracking can be more effective and simplified for a livestock farm or an agricultural producer by using RFID technology and corresponding electronic data storage/retrieval capabilities of today's modern information technology (IT) systems.

In case of livestock animals, such as cows and pigs, RFID tags are often attached to animals' ears or other body parts. Because these livestock animals are mobile and may exhibit certain sleeping habits which often place bending pressure on the exterior packaging of RFID tags, some RFID tags attached to livestock animals tend to experience premature failures. The premature failure rate of RED tags for livestock animals may become a significant issue as the usage of RFID tags become more ubiquitous in livestock farm industry.

In a typical device package (i.e. inlay) for an RFID tag, an RFID chip is bonded to an RFID antenna using adhesive materials (i.e. solder epoxy), which contains electrically conductive materials such as silver paste. The RFID antenna is typically metallic or conductive ink materials imprinted on a base substrate. During the manufacturing process of an RFID tag device package, it is difficult to control and/or accurately monitor viscosity, flux levels, and other physical properties of the adhesive materials dispensed to bonding contact points to prevent irregular or overflow of bonding adhesives. Typically, irregular or overflow of bonding adhesives weakens or even breaks the bonding of the RFID chip and the RFID antenna, if the RFID tag device package is subject to an external bending pressure.

Therefore, it may be desirable to devise an apparatus which enables quality assurance and reliability of each RFID tag by simulating external bending pressures. In addition, it may be desirable to devise a corresponding method to achieve quality assurance and reliability of RFID tags. Furthermore, it may be also desirable to make this apparatus optimized for a high-volume, manufacturing quality assurance environment.

SUMMARY

Summary and Abstract summarize some aspects of the present invention. Simplifications or omissions may have been made to avoid obscuring the purpose of the Summary or the Abstract. These simplifications or omissions are not intended to limit the scope of the present invention.

In one embodiment of the invention, an RFID tag-bending test apparatus configured to simulate external bending pressures on an RFID tag is disclosed. This apparatus comprises: a tag-bending station comprising one or more tag holding clips to hold the RFID tag, one or more clip joints to attach the one or more tag holding clips to a side rail of the tag-bending station, and a bending axis rod; an electrical motor configured to generate a rotational force, which is operatively transmitted to the tag-bending station to cause a squeezing action of the one or more tag holding clips on the RFID tag, wherein the squeezing action simulates the external bending pressures on the RFID tag; a control panel unit configured to control a bending test sequence, a bending speed, and a bending cycle counter of the tag-bending station; and a power supply unit configured to power the RFID tag-bending test apparatus, including the electrical motor and the control panel unit.

In another embodiment of the invention, a method of testing an RFID tag with an external bending pressure simulation using an RFID tag-bending test apparatus is disclosed. This method comprises the steps of securely placing one or more RFID tags in corresponding tag holding clips on the RFID tag-bending test apparatus; configuring the RFID tag-bending test apparatus using a control panel unit to adjust a bending speed, a number of bending cycles, and a bending test sequence for the one or more RFID tags; initiating the bending test sequence by activating an electrical motor of the RFID tag-bending test apparatus; and completing the bending test sequence for the one or more RFID tags based on a configured number of bending cycles by a user.

DETAILED DESCRIPTION

Figure 1:
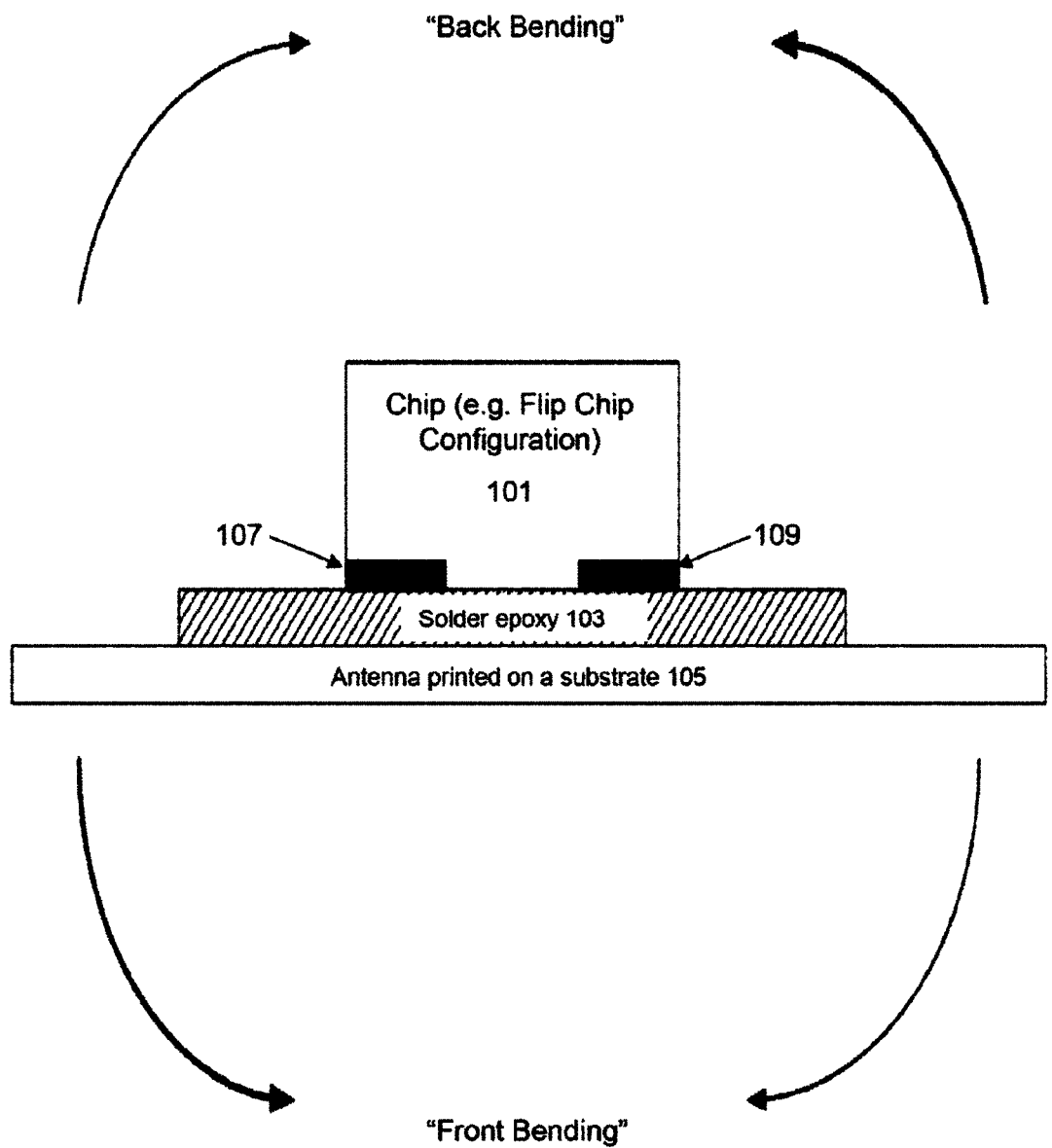
FIG. 1 shows a cross sectional diagram of an internal structure (i.e. inlay) of an RFID tag comprising an antenna printed on a base substrate, an RFID chip, and adhesive materials bonding the base substrate and the RFID chip.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

The detailed description is presented largely in terms of description of shapes, configurations, and/or other symbolic representations that directly or indirectly resemble one or more apparatuses and methods for RFID tag-bending testing, wherein the one or more apparatuses and methods are used for reliability checkup and quality assurance of RFID tags. These descriptions and representations are the means used by those experienced or skilled in the art to most effectively convey the substance of their work to others skilled in the art.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment. Furthermore, separate or alternative embodiments are not necessarily mutually exclusive of other embodiments. Moreover, any orders of blocks in process flowcharts or diagrams representing one or more embodiments of the invention do not inherently indicate any particular order nor imply any limitations in the invention.

For the purpose of describing the invention, a term "livestock" is defined as farm animals raised for use and/or profit. The term "livestock" can include, but are not limited to, cattle, sheep, pigs, goats, horses, donkeys, mules, and poultry (e.g. chickens, ducks, turkeys, and geese).

Furthermore, for the purpose of describing the invention, a term "adhesive material" or "adhesive materials" are defined as single or compound chemical substances, which can bond one electrical component (e.g. a solder bump of a flip chip-mounted RFID chip) to another component (e.g. a base substrate with an RF antenna). An adhesive material used for bonding a solder bump or a contact point of one electrical component (e.g. a flip chip-mounted RFID chip) with another electrical component (e.g. a base substrate) may also be called "solder epoxy" in one or more embodiments of the invention. Examples of solder epoxy include electrical conductive pastes such as silver paste and silver-tin compound paste.

In addition, for the purpose of describing the invention, a term "radio frequency identification," or RFID, is defined as a wireless signal-based identification of a wirelessly-accessible tag (e.g. an "RFID tag") using a wirelessly-accessible tag reader (e.g. an "RFID tag access module"). In a preferred embodiment of the invention, an RFID tag typically contains a non-volatile storage (e.g. a non-volatile memory unit, another data storage unit, and etc.) configured to be accessed by the RFID tag access module, an RF antenna (e.g. a UHF antenna module) operatively connected to the RFID tag access module, or another tag information access device for data retrieval (i.e. read function) or data storage (i.e. write function). Furthermore, examples of RFID tag access module include, but are not limited to, UHF (ultra high frequency) tag access modules and LF (low frequency) tag access modules.

In general, ultra high frequency (UHF) tag access modules are capable of achieving longer read/write ranges (e.g. up to several meters) and multiple RFID tag read/write capabilities, which were difficult to achieve in conventional low frequency (LF)-based RFID devices exhibiting shorter read/write ranges (e.g. approximately up to 30 centimeters) and single tag scan functionalities. In a preferred embodiment of the invention, the UHF range for the RFID tag access module is defined by ISO/IEC 18000-6 air interface standard, which utilizes an operating frequency range of 860 MHz~960 MHz. In another embodiment of the invention, the UHF operating frequency range may be defined more broadly as 300 MHz~3 GHz. In general, the conventional LF operating frequencies are below the UHF RFID tag access module operating frequency ranges.

Figures 3, 4:
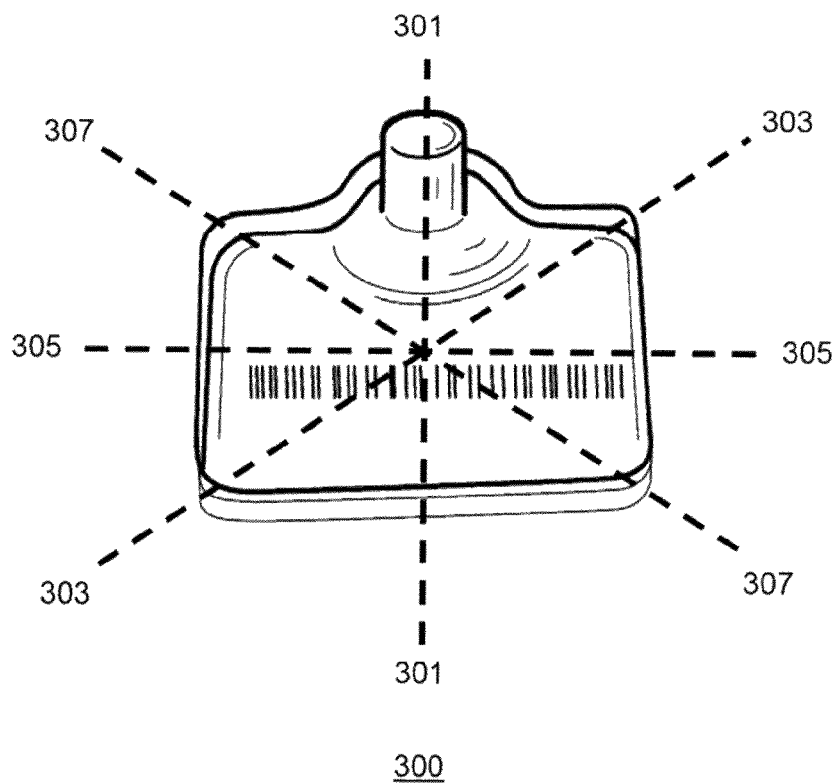
FIG. 3 shows an example of an RFID tag package with perforated lines for various bending axes, in accordance with an embodiment of the invention.
FIG. 4 shows a table containing number of defective RFID tags per 100 RFID tags and corresponding RFID tag defective rate percentages with respect to various bending axes, in accordance with an embodiment of the invention.
Figure 6:
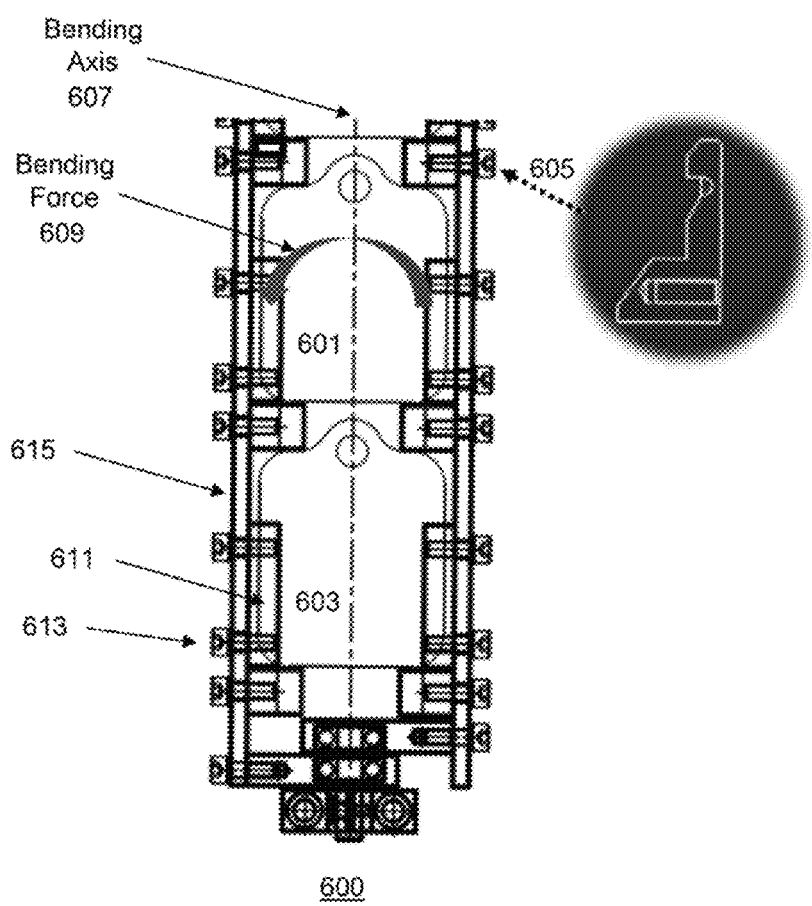
FIG. 6 shows a partial view of a tag-bending station, which includes tag holding clips positioning RFID tags to their vertical bending axis in an RFID tag-bending test apparatus, in accordance with an embodiment of the invention.
Figure 7:
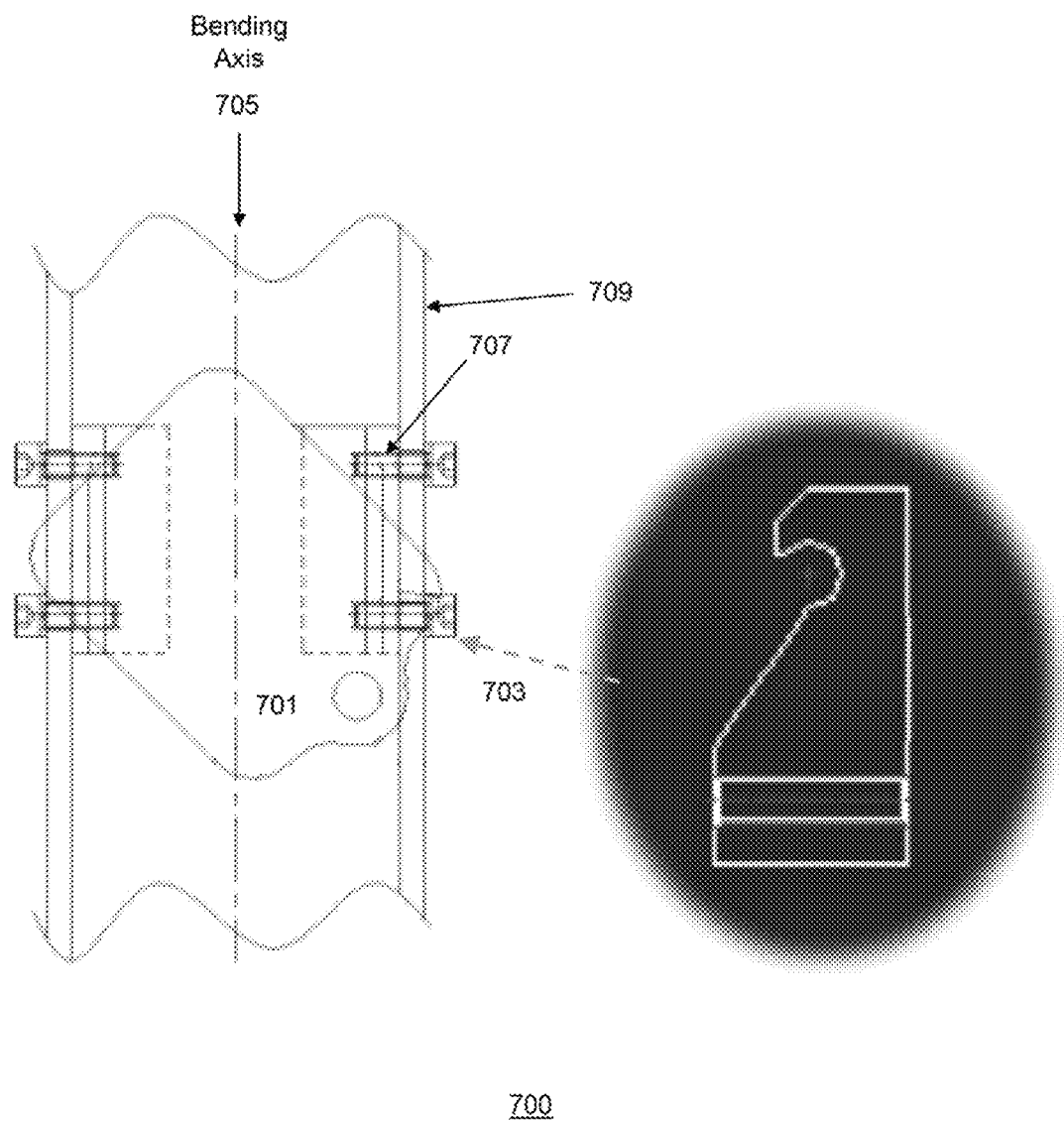
FIG. 7 shows a partial view of a tag-bending station, which includes tag holding clips positioning an RFID tag to its diagonal bending axis in an RFID tag-bending test apparatus, in accordance with an embodiment of the invention.

Furthermore, for the purpose of describing the invention, a term "bending axis" is defined as a line about which parts of an RFID tag bends forward or backward on an RFID tag-bending test apparatus. Examples of various bending axes are shown in FIG. 3. Examples of a particular bending axis for bending parts of an REND tag are also shown in FIG. 6 and FIG. 7.

In addition, for the purpose of describing the invention, a term "bending force" is defined as bending pressure exerted on one or more parts of an RFID tag. In real life applications of RFID tags on livestock animals, the bending forces may be caused by livestock animals' mobile and sleeping habits. In one or more embodiments of the invention, the bending forces may be exerted by tag holding clips to RFID tags tested on an RFID tag-bending test apparatus.

Moreover, for the purpose of describing the invention, a term "tag holding clip" is defined as a device with one or more anchors to hold an RFID tag securely for a particular bending position (e.g. vertical, diagonal, and etc.). In a preferred embodiment of the invention, the one or more anchors are custom-shaped to hold an RFID tag at a particular bending position during a bending test sequence performed on an RFID tag-bending test apparatus.

One aspect of an embodiment of the present invention is providing an RFID tag-bending test apparatus configured to execute a bending test sequence on RFID tags for quality assurance and reliability testing of recently-manufactured RFID tags. In one embodiment of the invention, the bending test sequence may exert repeated bending pressures on one or more bending axes to simulate bending pressures exerted by livestock animals. Malfunctioning RFID tags which fail to operate properly after the bending test sequence can be excluded from other RFID tags which pass the bending test sequence to minimize defective rates of RFID tags offered for sale to customers.

Another aspect of an embodiment of the present invention is providing a method to conduct a bending test sequence to achieve quality assurance of recently-manufactured RFID tags by identifying malfunctioning RFID tags under bending pressures.

Yet another aspect of an embodiment of the present invention is identifying one or more bending axes which make an RFID tag most prone for malfunctioning.

Furthermore, another aspect of an embodiment of the present invention is devising a bending orientation-specific custom-shaped hook for a tag holding clip, wherein the bending orientation-specific custom-shaped hook is configured to provide a secure position for an RFID tag undergoing a bending test sequence.

In addition, another aspect of an embodiment of the present invention is providing an RFID tag-bending test apparatus optimized for batch testing (i.e. a group testing) of RFID tags using one or more bending test sequences.

FIG. 1 shows a cross sectional diagram (100) of an internal structure (i.e. inlay) of one example of an RFID tag. In this particular example, the cross section diagram shows an RF antenna printed on a base substrate (105), an RFID chip (101) embedding a non-volatile memory unit, and adhesive materials called "solder epoxy" (103), which bonds the base substrate and the RFID chip together.

In case of a passive (i.e. battery-less or battery free) tag, the non-volatile memory unit in the RFID chip (101) can be energized and accessed for data reading and/or writing via electromagnetic induction from an RFID reader. In case of an active (i.e. internally battery-powered) tag, the non-volatile memory unit in the RFID chip (101) can be powered by an internal battery source and correspond to an external read or write request from an RFID reader.

Furthermore, in the example shown in FIG. 1, the solder epoxy (103) may be placed between one or more solder bumps or contact points (107, 109) of the RFID chip (101) and corresponding contact points on the base substrate (105). The RFID chip (101) may utilize a flip-chip mounting configuration, as shown in FIG. 1, and have one or more solder bumps or contact points (107, 109) bonded to corresponding contact points on the base substrate (105) using the solder epoxy (103). The solder epoxy (103) is typically electrically conductive and may comprise materials of high electrical conductivity, such as silver paste, silver-tin paste, or other materials with desirable characteristics depending on a need of a particular implementation.

Continuing with FIG. 1, an RFID tag is often subject to external bending pressures if it is attached to a livestock animal's body part (e.g. an ear of the livestock animal). The livestock animal's mobility and sleeping habits may bend the RFID tag occasionally or frequently. As shown in the RFID tag internal cross section (100) in FIG. 1, an external bending pressure may be "front bending" or "back bending." Because the solder epoxy (103) and solder bumps (e.g. 107, 109) of the RFID chip (101) are not generally very flexible materials once they are bonded to the base substrate (105), significant bending pressure to the inner parts of the RFID tag may cause breakage of contact points, bonding, and/or electrical connections, which results in premature failure of the RFID tag.

The RFID tag is particularly vulnerable to breakage of bonding among the internal structural elements (e.g. 101, 103, and 105), if the solder epoxy (103) is formulated and/or dispensed incorrectly during a bonding process of the RFIC chip (101) to the base substrate (105). Because it is difficult to monitor and control viscosity, flux levels, and other physical properties of the solder epoxy (103) very accurately during the bonding process, it is not uncommon to have irregularly-shaped or overflowed solder epoxy (103) around the solder bumps (e.g. 107, 109) of the RFID chip (101) and the corresponding contact points on the base substrate (105).

Figure 2:
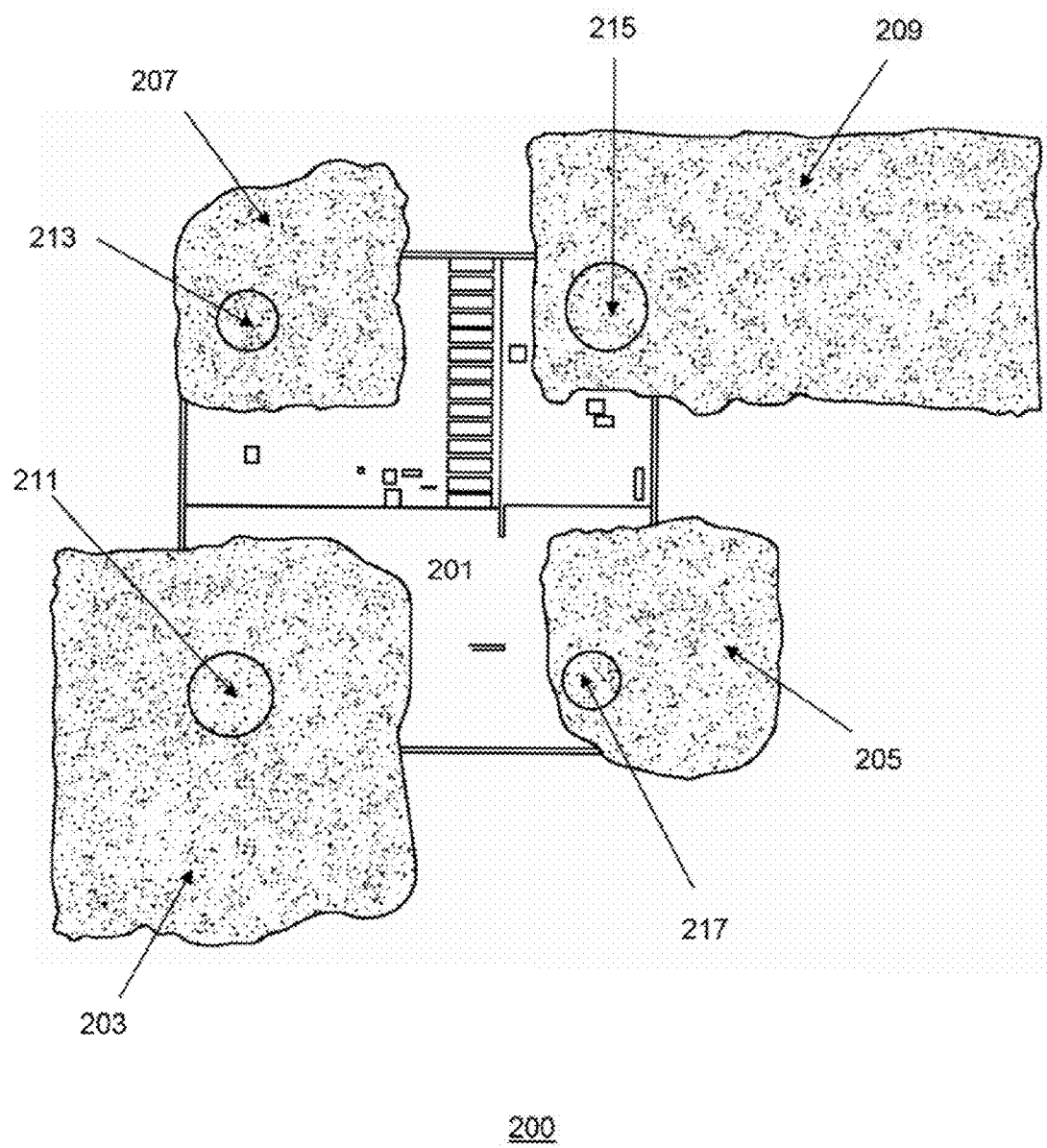
FIG. 2 shows an example of irregular and overflowed adhesive materials on contact points (e.g. flip-chip solder bumps) of an RFID chip, wherein the adhesive materials are used for attachment of the contact points to a base substrate.

FIG. 2 shows an example (200) of irregular and/or overflowed adhesive materials (i.e. solder epoxy areas (203, 205, 207, 209)) on contact points (i.e. flip-chip solder bumps (211, 217, 213, 215) of an RFID chip (201)), wherein the adhesive materials are used for attachment of the contact points to a base substrate (e.g. 105 in FIG. 1). In this particular example (200), a first solder epoxy area (203) embedding a first solder bump (211) is significantly larger than a second solder epoxy area (205) embedding a second solder bump (217) and a third solder epoxy area (207) embedding a third solder bump (213). Similarly, a fourth solder epoxy area (209) embedding a fourth solder bump (215) is substantially larger than the other three epoxy areas (203, 205, 207) in this particular example.

Typically, irregularity and/or overflow of adhesive materials (e.g. silver paste or another solder epoxy) dispensed on a particular solder bump during a bonding process may cause a solder epoxy area to be enlarged or irregularly shaped. Because it is difficult to monitor and control viscosity, flux levels, and other physical properties of adhesive materials very accurately during the bonding process, it is not uncommon to have irregularly-shaped or overflowed solder epoxy areas (e.g. the first solder epoxy area (203), the fourth solder epoxy area (209)). The enlarged and irregularly-shaped solder epoxy areas (e.g. 203, 209) typically receive more bending stress than smaller epoxy areas (e.g. 205, 207) under an external bending pressure on an RECD tag package, thereby causing potential breakage of the bonded elements (e.g. 107, 103, and 105 of FIG. 1) and a premature failure of the RFID tag. In a typical mass-production RFID tag manufacturing environment, conventional quality assurance tests do not easily detect undesirable irregularity and enlargement of epoxy areas during or after the bonding process. Therefore, one or more embodiments of the present invention disclosing an RFID tag-bending test apparatus and an associated bending test sequence as novel quality assurance measures (i.e. for efficient identification of failure-prone RFID tags) are highly desirable for RFID tags in livestock applications.

FIG. 3 shows an example of an RFID tag package (300) with perforated lines for various bending axes, in accordance with an embodiment of the invention. In this particular example, a vertical bending axis (301), a first diagonal bending axis (303), a horizontal bending axis (305), and a second diagonal bending axis (307) are shown. A particular bending axis indicates a line about which parts of the RFID tag package (300) bends forward or backward due to an external bending pressure caused, for example, by a livestock animal or an RFID tag-bending test apparatus disclosed in various embodiments of the present invention.

FIG. 4 shows a table (400) containing number of defective RFID tags per 100 RFID tags and corresponding RFID tag defective rate percentages with respect to various bending axes, in accordance with an embodiment of the invention. In this particular example, a sample of 100 RFID tags was tested for each row in the table (400), for a total of 800 RFID tags for this experiment. Each batch of 100 RFID tags was bent forward or backward (i.e. "Front/Back" column in the table (400)) along a particular bending axis (i.e. "Direction" column in the table (400)). Then, the functionality of each RFID tag was checked to determine the number of defective tags (i.e. "Defective Tag" column) and the defective rate (i.e. "Defective Rate" column).

In this particular experiment as shown in the table (400), the front-bending of RFID tags resulted in higher defective rates than the back-bending of RFID tags. Furthermore, the front-bending involving a vertical bending axis (e.g. 301 of FIG. 3) and two diagonal bending axes (e.g. 303, 307 of FIG. 3) resulted in substantially higher defective rates (i.e. 28.0%, 24.0%, and 22.0%, respectively) than the front-bending around the horizontal axis (i.e. 1.0%) in this particular experiment. The result of this experiment shown in FIG. 4 is particular to one RFID tag design, and therefore does not limit other outcomes involving front/back orientation and various bending axes, if another RFID tag design with different internal structures and/or packaging is used for a similar experiment. However, experiments similar to one shown in table (400) of FIG. 4 may be used to derive and optimize a bending test sequence on an RFID tag-bending test apparatus of the present invention for a particular RFID tag design.

Figure 5:
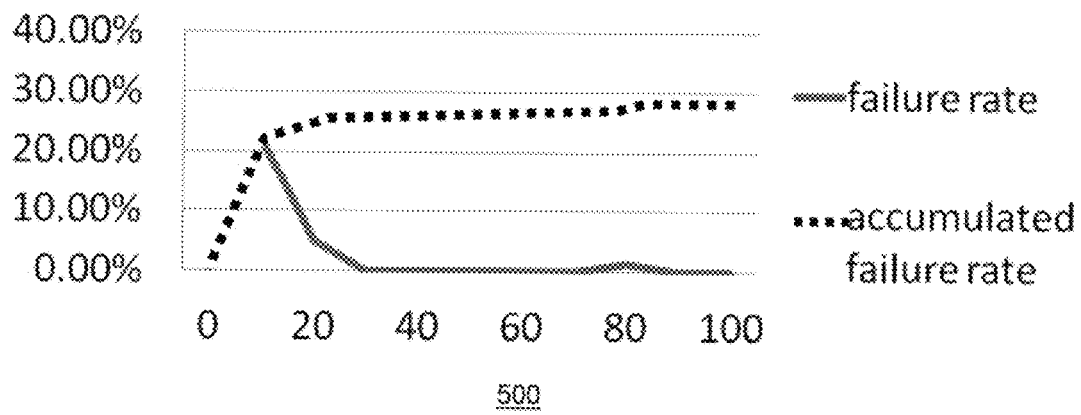
FIG. 5 shows a graph showing failure rates and accumulated failure rates of a plurality of RFID tags against a number of bending test operations, in accordance with an embodiment of the invention.

FIG. 5 shows a graph (500) showing failure rates and accumulated failure rates of a plurality of RFID tags against a number of bending test operations, in accordance with an embodiment of the invention. The failure rate shown as a solid downward curve in the graph (500) indicates a probability of an RFID tag failure as more bending test operations are performed on that particular RFID tag. In this particular example shown in graph (500), the failure rate of the particular RFID tag becomes minimal or nearly zero as more than 30 bending test operations are performed on that particular RFID tag. Furthermore, the accumulated failure rate of a group of RFID tags used for this experiment reaches a plateau (i.e. a nearly flat line) after about 20 bending test operations per RFID tag. Therefore, this experiment suggests that defective RFID tags (e.g. due to irregularity or overflow of adhesive materials during the bonding process) tend to show up early in repeated bending test operations. As shown in the graph (500), because RFID tags that are likely to fail due to bending pressure fail relatively early in a bending test sequence, and because the accumulated failure rates of the group of RFID tags tend to be flat-lined after a certain number of bending test operations, a novel tag-bending test apparatus disclosed in various embodiments of the present invention is likely to be particularly useful in quality assurance and reliability testing of RFID tags.

FIG. 6 shows a partial view of a tag-bending station (600), which includes tag holding clips (e.g. 611) positioning RFID tags (e.g. 601, 603) to their vertical bending axis in an RFID tag-bending test apparatus in accordance with an embodiment of the invention. In a preferred embodiment of the invention, each tag holding clip (e.g. 611) is attached to a side rail (615) of a tag-bending station by one or more clip joints (e.g. 613). Furthermore, in the preferred embodiment of the invention, the RFID tag-bending test apparatus applies a bending force (609) around a bending axis (607), which partially bends a first RFID tag (601) and a second RFID tag (603) per bending test operation.

In one or more embodiments of the invention, a bending test sequence comprises a plurality of bending test operations, wherein each bending test operation comprises asserting a single cycle of bending force from the RFID tag-bending test apparatus. For example, if a series of thirty front-bending test operations are performed to an RFID tag, then it may be called a "bending test sequence" comprising thirty front-bending test operations. The first RFID tag (601) and the second RFID tag (603) may undergo one or more bending test sequences.

As shown in a cross-section (605) of a tag holding clip in FIG. 6, in one or more embodiments of the invention, each tag holding clip has a bending orientation-specific custom-shaped hook to hold an RFID tag securely during a bending test sequence. In the partial view of the tag-bending station (600) shown in FIG. 6, each RFID tag can be bent around its vertical bending axis (e.g. 301 of FIG. 3) because the bending axis (607) of the RFID tag-bending test apparatus overlaps the vertical bending axis (e.g. 301 of FIG. 3) of each RFID tag. In some embodiments of the invention, RFID tags may be positioned or oriented differently relative to their corresponding tag holding clips (e.g. 611) to accommodate bending test operations around a diagonal bending axis (e.g. 303, 307 of FIG. 3) or a horizontal bending axis (e.g. 305 of FIG. 3).

Furthermore, in some embodiments of the invention, tag holding clips (e.g. 611) may be adjustable to accommodate various sizes of RFID tags. In other embodiments of the invention, tag holding clips of different dimensions and varying sizes may be used to accommodate various sizes of RFID tags.

FIG. 7 shows a partial view of a tag-bending station (700), which includes tag holding clips (e.g. 707) positioning an RFID tag (701) to its diagonal bending axis in an RFID tag-bending test apparatus in accordance with an embodiment of the invention. In a preferred embodiment of the invention, each tag holding clip (e.g. 707) is attached to a side rail (709) of a tag-bending station by one or more clip joints. In FIG. 7, the RFID tag (701) is rotated to position the bending axis (705) of the RFID tag-bending test apparatus along a diagonal bending axis (e.g. 303 or 307 of FIG. 3) of the RFID tag (701).

Furthermore, in the preferred embodiment of the invention, the RFID tag-bending test apparatus applies a bending force around the bending axis (705), which partially bends the RFID tag (701) per bending test operation. In one or more embodiments of the invention, a bending test sequence comprises a plurality of bending test operations, wherein each bending test operation comprises asserting a single cycle of bending force from the RFID tag-bending test apparatus. For example, if a series of forty front-bending test operations are performed to an RFID tag, then it may be called a "bending test sequence" comprising forty front-bending test operations. The RFID tag (701) may undergo one or more bending test sequences along its diagonal bending axis overlapped by the bending axis (705) of the RFID tag-bending test apparatus, as shown in FIG. 7.

As shown in a cross-section (703) of a tag holding clip in FIG. 7, in one or more embodiments of the invention, each tag holding clip has a bending orientation-specific custom-shaped hook to hold an RFID tag securely during a bending test sequence. In the partial view of the tag-bending station (700) shown in FIG. 7, the RFID tag (70.1) can be bent around its diagonal bending axis (e.g. 303 or 307 of FIG. 3) because the bending axis (705) of the RFID tag-bending test apparatus overlaps the diagonal bending axis of the RFID tag (701). In some embodiments of the invention, RFID tags may be positioned or oriented differently relative to their corresponding tag holding clips (e.g. 707) to accommodate bending test operations around a vertical bending axis, as shown previously in FIG. 6, or a horizontal bending axis, as shown by a horizontal bending axis (305) in FIG. 3.

Furthermore, in some embodiments of the invention, tag holding clips (e.g. 707) may be adjustable to accommodate various sizes of RFID tags. In other embodiments of the invention, tag holding clips of different dimensions and varying sizes may be used to accommodate various sizes of RFID tags.

Figure 8:
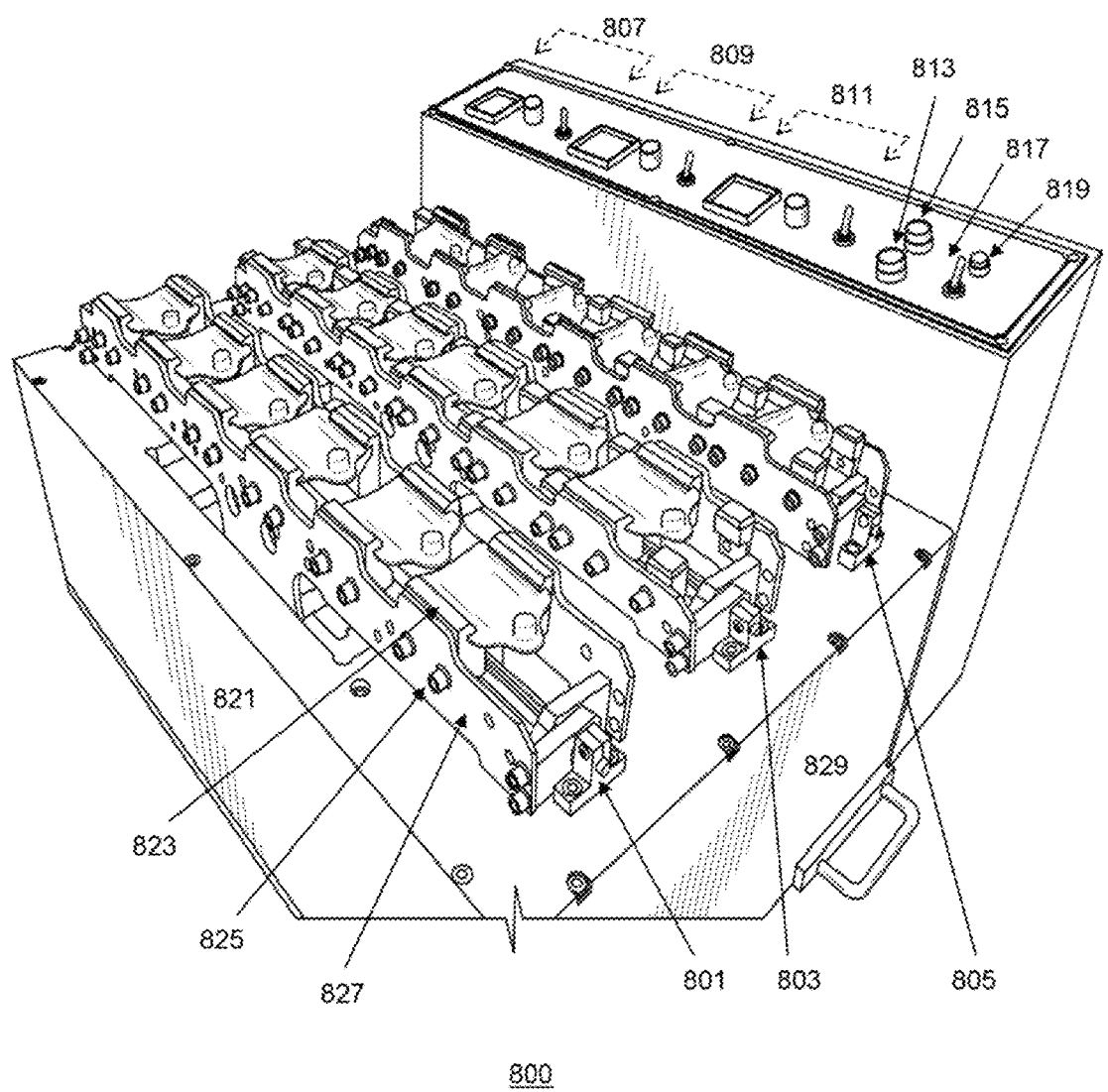
FIG. 8 shows a perspective view of an RFID tag-bending test apparatus, in accordance with an embodiment of the invention.

FIG. 8 shows a perspective view of an RFID tag-bending test apparatus (800), in accordance with an embodiment of the invention. In a preferred embodiment of the invention, the RFID tag-bending test apparatus (800) comprises a first tag-bending station (801), a second tag-bending station (803), a third tag-bending station (805), a control panel unit (807, 809, 811, 813, 815, 817, 819), an electrical motor per tag-bending station to provide cyclical bending forces along bending axes, a power supply unit to power the RFID tag-bending test apparatus, and various connecting rods, joints, and pistons to transfer the rotational force from the electrical motor to each tag-bending station (i.e. 801, 803, 805). In addition, in the preferred embodiment of the invention, an RFID tag-bending test apparatus casing (e.g. 821, 829) encapsulates the electrical motors, the power supply unit, and a large portion of the various connecting rods, joints, and pistons for transfer of the rotational force from the electrical motors to the tag-bending stations (i.e. 801, 803, 805).

Furthermore, in the preferred embodiment of the invention, each tag-bending station (i.e. 801, 803, 805) comprises one or more tag holding clips (823), one or more clip joints (825) to attach the one or more tag holding clips (823) to a side rail (827) of a tag-bending station, one or more RFID tags securely placed in the one or more tag holding clips (823), and a bending axis rod (e.g. 905 of FIG. 9) to transform the rotational force of the electrical motor into a cyclical bending force exerted on the one or more RFID tags securely placed in the one or more tag holding clips (823). Moreover, in some embodiments of the invention, tag holding clips (e.g. 823) may be adjustable to accommodate various sizes of RFID tags. In other embodiments of the invention, tag holding clips of different dimensions and varying sizes may be used to accommodate various sizes of RFID tags.

As shown in FIG. 8, in one embodiment of the invention, RFID tags placed in the first and the second tag-bending stations (801, 803) are positioned to undergo a bending test sequence along their vertical bending axes (e.g. 301 of FIG. 3), while some of the RFID tags placed in the third tag-bending station (805) are positioned to undergo the bending test sequence along their diagonal bending axes (e.g. 303 of FIG. 3). In another embodiment of the invention, RFID tags in the tag-bending stations may be oriented in other directions of bending (i.e. vertical, diagonal, horizontal, and etc.) in order to optimize effectiveness of a tag-bending test as a quality assurance procedure for a particular design of an RFID tag package.

Continuing with FIG. 8, in a preferred embodiment of the invention, the control panel unit (807, 809, 811, 813, 815, 817, 819) comprises a first tag-bending station control unit (807), a second tag-bending station control unit (809), a third tag-bending station control unit (811), a master stop button (813), a master start button (815), a main power on/off switch (817), and a main power on/off indicator (819). Furthermore, in the preferred embodiment of the invention, each of the tag-bending station control unit (807, 809, 811) may comprise an electric motor on/off switch per station, a speed adjustment knob per station, and a bending test counter per station. In the preferred embodiment of the invention, a user is able to configure or program each tag-bending station (801, 803, 805) to set a particular tag-bending station's own bending test sequence, speed, and counter, independent of tag bending sequences, speeds, and counters of other tag-bending stations in the RFID tag-bending test apparatus. In one embodiment of the invention, the speed of a tag-bending station may be configured to be fixed or variable, depending on a particular bending test sequence. Furthermore, in one embodiment of the invention, the bending test counter per station may increment its count by one, when a single cycle of bending force is exerted on RFID tags placed in a particular tag-bending station.

In some embodiments of the invention, it may be desirable to include an RFID reader attached to or located near the RFID tag-bending test apparatus casing (e.g. 821, 829), so that defective RFID tags after a bending test sequence can be readily identified among all tested RFID tags, even before each RFID tag is removed from the RFID tag-bending test apparatus (800). The inclusion of an RFID reader to the RFID tag-bending test apparatus to perform test read/write operations to RFID tags after completion of the bending test sequence may further improve efficiency of quality assurance and reliability testing procedures. In other embodiments of the invention, the RFID tag-bending test apparatus (800) does not include an RFID reader. In these embodiments of the invention, RFID tags may need to be removed from the corresponding tag holding clips in each tag-bending station, and then transported to a separate RFID tag function check tester.

In addition, in the preferred embodiment of the invention, the master stop button (813) is designed to stop all functions of the RFID tag-bending test apparatus (800). Similarly, the master start button (815) is designed to activate all functions of the RFID tag-bending test apparatus (800) as configured by the user for each tag-bending station. The main on/off power switch (817) is designed to turn main electrical power on or off to the RFD tag-bending test apparatus (800). Moreover, the main power on/off indicator (819) is configured to show whether the main electrical power to the RFID tag-bending test apparatus (800) is on or off.

Furthermore, in the preferred embodiment of the invention, the operational power for the RFID tag-bending test apparatus utilizes 220V AC electrical outlet, and each electrical motor used per tag-bending station may consume up to 90 Watts of power at a maximum speed. In other embodiments of the invention, a different AC electrical outlet or a DC power source may be utilized. Similarly, larger-capacity or smaller-capacity electrical motors may be used in other embodiments of the invention, depending on the needs of a particular design requirement for an RFID tag-bending test apparatus.

Figure 9:
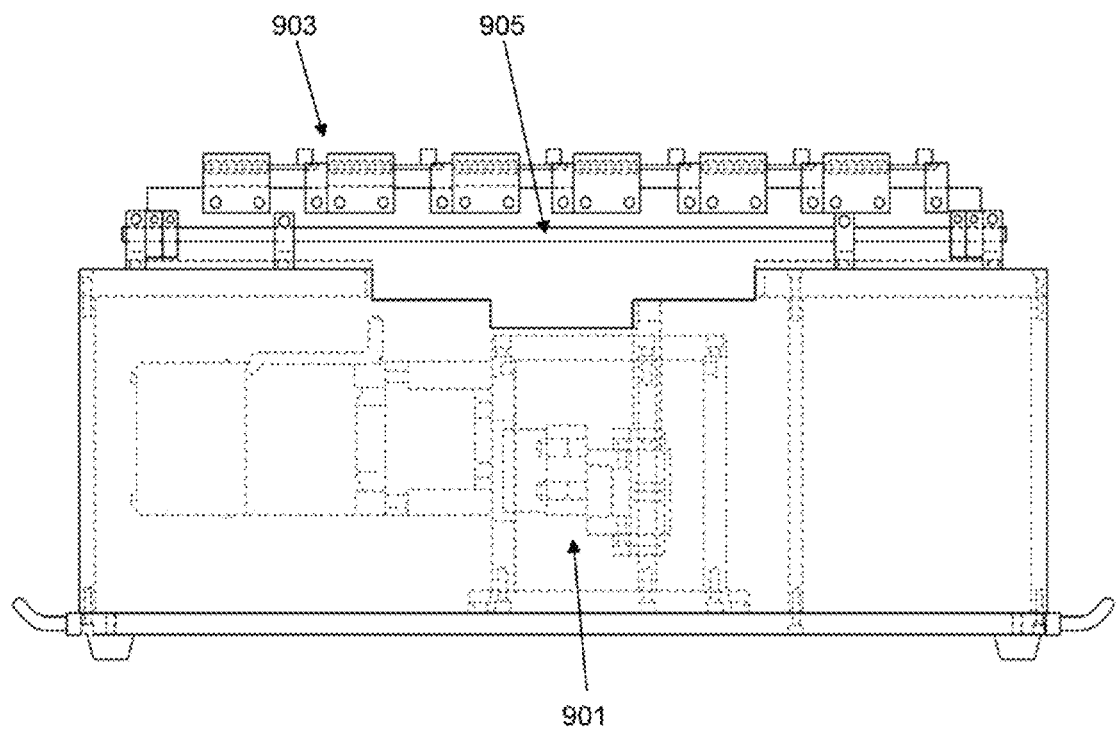
FIG. 9 shows a first side view of an RFID tag-bending test apparatus in accordance with an embodiment of the invention.

FIG. 9 shows a first side view (821) of an RFID tag-bending test apparatus in accordance with an embodiment of the invention. In this embodiment of the invention as shown in FIG. 9, the RFID tag-bending test apparatus contains a tag-bending station motor (901). The tag-bending station motor (901) is configured to generate a rotational force which can be operatively transmitted to a tag-bending station (903) as a bending force exerted to RFID tags in tag holding clips (e.g. 823 of FIG. 8). In a preferred embodiment of the invention, the transformation of force from the rotational force to the bending force is achieved by various connecting rods, joints, and/or pistons operatively connecting the tag-bending station motor (901) to the tag holding clips (e.g. 823 of FIG. 8) of the tag-bending station (903).

In the preferred embodiment of the invention, the tag holding clips (e.g. 823 of FIG. 8) attached to the side rails (e.g. 827 of FIG. 8) of the tag-bending station (903) effectively exert a cyclical (i.e. periodically-occurring) bending force to each RFID tag placed in the tag holding clips (e.g. 823 of FIG. 8) by creating a squeezing action. In the preferred embodiment of the invention, a bending axis rod (905) serves as an axis of partial rotation for the side rails (e.g. 827 of FIG. 8) and the tag holding clips (e.g. 823 of FIG. 8) in the tag-bending station (903).

Figure 10:
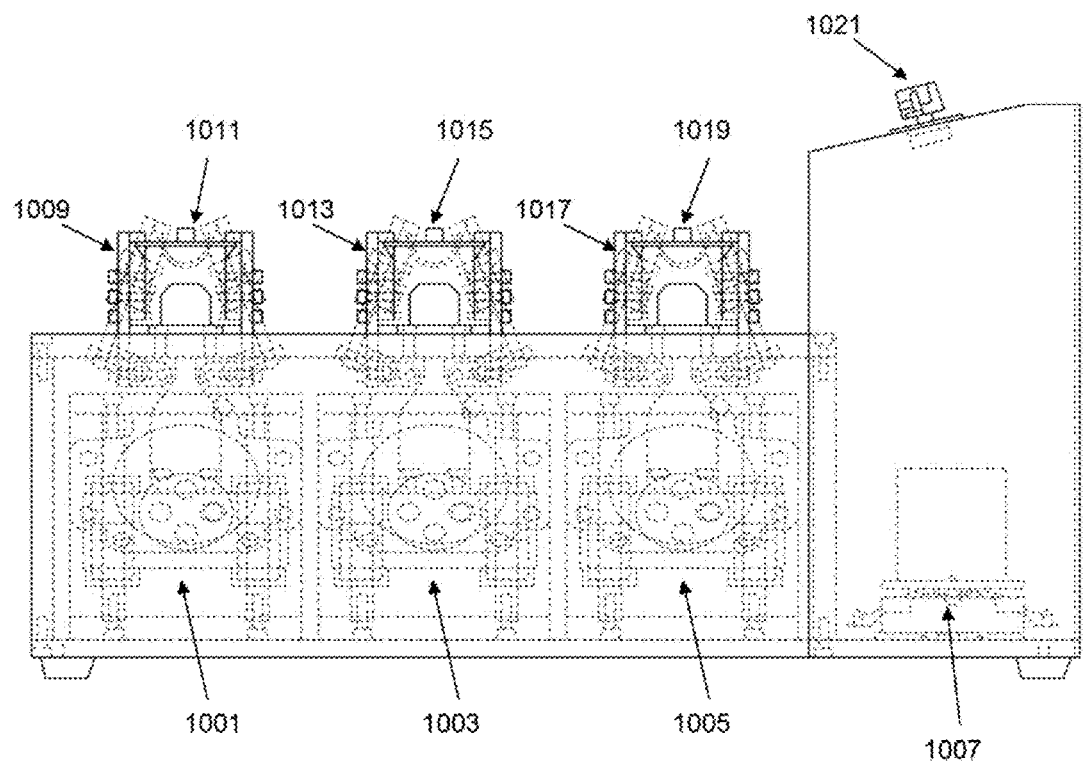
FIG. 10 shows a second side view of an RFID tag-bending test apparatus in accordance with an embodiment of the invention.

FIG. 10 shows a second side view (829) of an RFID tag-bending test apparatus in accordance with an embodiment of the invention. In this embodiment of the invention as shown in FIG. 10, the RFID tag-bending test apparatus contains a tag-bending station motor per each tag-bending station for a total of three tag-bending station motors (1001, 1003, 1005). Each of the tag-bending station motors (1001, 1003, 1005) is configured to generate a rotational force, which can be operatively transmitted to its corresponding tag-bending station as a bending force exerted to an RFID tag (1011, 1015, or 1019) securely held in tag holding clips (1009, 1013, or 1017). In a preferred embodiment of the invention, the transformation of force from the rotational force to the bending force is achieved by various connecting rods, joints, and/or pistons operatively connecting a particular tag-bending station motor (1001, 1003, or 1005) to its corresponding tag holding clips (1009, 1013, or 1017) for a particular tag-bending station.

In the preferred embodiment of the invention, the tag holding clips (1009, 1013, or 1017) attached to the side rails of a particular tag-bending station among the three tag-bending stations effectively exert a cyclical (i.e. periodically-occurring) bending force to each RFID tag (1011, 1015, or 1019) placed in the tag holding clips (1009, 1013, or 1017) of the particular tag-bending station by creating a squeezing action, as shown by perforated lines in FIG. 10. The perforated lines in each of the three tag-bending stations shown in FIG. 10 show an outline of a tag-bending station motor (1001, 1003, or 1005) per tag-bending station. The perforated lines also show at least some outlines of various connecting rods, joints, and/or pistons operatively connecting each tag-bending station motor (1001, 1003, or 1005) to its corresponding tag holding clips (1009, 1013, or 1017) for one or more embodiments of the invention. In addition, the perforated lines partially overlapping the solid lines for the tag holding clips (1009, 1013; or 1017) outline the squeezing action of the tag holding clips on RFID tags (1011, 1015, or 1019), which can be bent downward under the bending pressure, as shown by perforated lines in FIG. 10. In one embodiment of the invention, the squeezing action of the tag holding clips can support a bending angle between 0 degrees and +45 degrees, and between 0 degrees and −45 degrees, from a vertical position (i.e. rest position) of a tag holding clip to a fully-bent position of the tag holding clip.

In a preferred embodiment of the invention, the squeezing action of the tag holding clips (e.g. 1009, 1013, 1017) can be generated by cyclically elevating and lowering of pistons, wherein each piston is positioned between a pair of tag holding clips (e.g. 1009, 1013, or 1017) and above each tag-bending station motor (e.g. 1001, 1003, 1005). Furthermore, in the preferred embodiment of the invention, a "bottom portion" of the tag-bending test apparatus may comprise tag-bending station motors (e.g. 1001, 1003, 1005), various connecting rods, joints, and/or pistons. In this preferred embodiment of the invention, a "top portion" of the tag-bending test apparatus may comprise tag holding clips (e.g. 1009, 1013, 1017), side rails (e.g. 827 of FIG. 8), and clip joints (e.g. 825 of FIG. 8). It may be desirable to implement the top portion and the bottom portion of the tag-bending test apparatus to be not physically jointed together for a higher level of test apparatus reliability and maintenance. In the preferred embodiment of the invention, the rotational force from each tag-bending station motor may raise or lower each piston, which changes the angle and the position of each pair of tag holding clips (e.g. 1009, 1013, 1017) to cause the squeezing action on each RFID tag (e.g. 1011, 1015, 1019) placed in the tag holding clips (e.g. 1009, 1013, 1017). However, in another embodiment of the invention, the top portion and the bottom portion of the tag-bending test apparatus may be physically jointed together.

Continuing with FIG. 10, the tag-bending test apparatus also contains a power supply unit (1007) and a control panel unit (102.1) in one embodiment of the invention. The power supply unit (1007) can be configured to receive an external AC or DC electrical power, and can supply a desirable amount of electrical power to the tag-bending station motors (1001, 1003, 1005) and the control panel unit (1021). In a preferred embodiment of the invention, the power supply unit (1007) operates with an 220V AC external power outlet, and each of the tag-bending station motors (1001, 1003, 1005) consumes up to 90 Watts of electrical power at a maximum speed.

Figure 11:
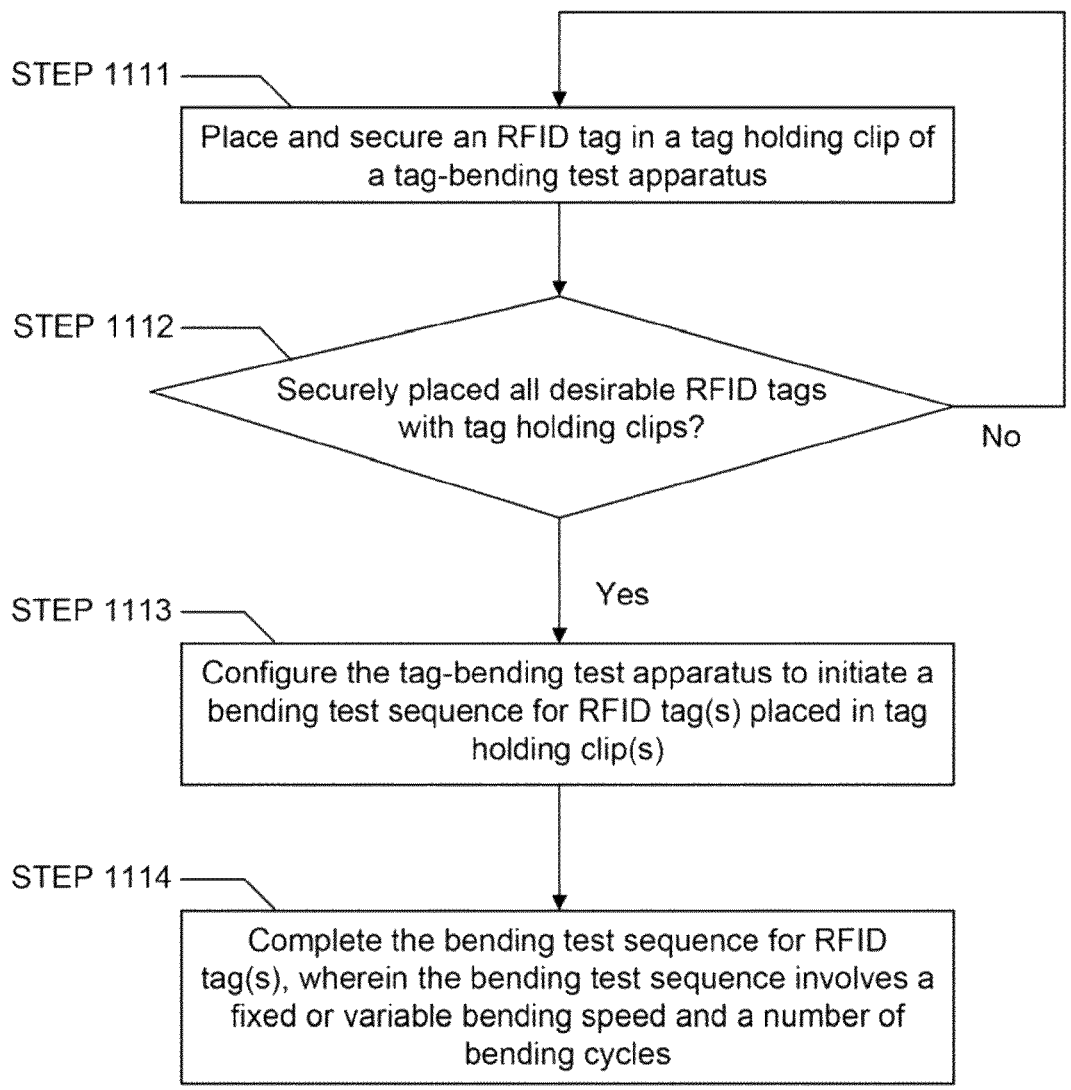
FIG. 11 shows a method of using an RFID tag-bending test apparatus in accordance with an embodiment of the invention.

FIG. 11 shows a method (1100) of using an RFID tag-bending test apparatus in accordance with an embodiment of the invention. In a preferred embodiment of the invention, a user or a machine first places and secures an RFID tag in a tag holding clip of an RFID tag-bending test apparatus, as shown in STEP 1111. The user or the machine then repeatedly places and secures other RFID tags in tag holding clips until all RFID tags to be tested are correctly placed in the RFID tag-bending test apparatus, as shown in STEP 1112. In a preferred embodiment of the invention, the RFID tag-bending test apparatus has three tag-bending stations, each of which is powered by a tag-bending station motor. In another embodiment of the invention, the RFID tag-bending test apparatus may have only a single tag-bending station or a multiple number of tag-bending stations other than three tag-bending stations, depending on a user's testing capacity needs for RFID tags.

Then, the user can configure the RFID tag-bending test apparatus to initiate a bending test sequence for RFID tags placed in the tag holding clips, as shown in STEP 1113. User configuration of the RFID tag-bending test apparatus may include, but are not limited to, a speed adjustment, a bending test sequence adjustment, and a target counter adjustment for one or more tag-bending stations in the RFID tag-bending test apparatus. Once the user has configured the RFID tag-bending test apparatus as desired, the bending test sequence for the one or more tag-bending stations can be executed for the RFID tags placed in the tag holding clips, wherein the bending test sequence may involve a fixed or variable bending speed and a preset number of bending cycles based on the configuration of the target counter adjustment, as shown in STEP 1114.

Various embodiments of the present invention disclosing an RFID tag-bending test apparatus and a related method of using the RFID tag-bending test apparatus may provide several advantages over conventional solutions. First, by identifying a bending axis (e.g. diagonal, vertical, and etc.) and a direction of bending (e.g. front bending, back bending) which make an RFID tag package particularly susceptible to premature failure, various embodiments of the present invention enable more effective quality assurance and reliability testing procedures for RFID tag packages, as shown and described, for example, by FIGS. 3~5. Second, quality assurance and reliability of recently-manufactured RFID tags may be substantially improved by utilizing a novel RFID tag-bending test apparatus and a related method of use disclosed in various embodiments of the present invention, which simulate external bending pressures to RFID tags with adjustable bending speeds, adjustable bending cycles, and adjustable RFID tag orientations to test for a particular bending axis, as shown and described, for example, by FIGS. 6~11. Furthermore, by utilizing a multiple number of tag-bending stations which accommodate batch testing of a large number of RFID tags in some embodiments of the present invention, the novel RFID tag-bending test apparatus can be optimized for a high-volume, manufacturing quality assurance environment.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An RFID tag-bending test apparatus configured to simulate external bending pressures on an RFID tag, the apparatus comprising:

a tag-bending station comprising one or more tag holding clips to hold the RFID tag, one or more clip joints to attach the one or more tag holding clips to a side rail of the tag-bending station, and a bending axis rod;

an electrical motor configured to generate a rotational force, which is operatively transmitted to the tag-bending station to cause a squeezing action of the one or more tag holding clips on the RFID tag, wherein the squeezing action simulates the external bending pressures on the RFID tag;

a control panel unit configured to control a bending test sequence, a bending speed, and a bending cycle counter of the tag-bending station;

a power supply unit configured to power the RFID tag-bending test apparatus, including the electrical motor and the control panel unit; and various connecting rods, joints, and pistons located between the electrical motor and the tag-bending station, wherein the various connecting rods, joints, and pistons transfer the rotational force from the electrical motor to the tag-bending station.

2. The RFID tag-bending test apparatus of claim 1, wherein each of the one or more tag holding clips includes a bending orientation-specific custom-shaped hook to provide a secure position for an RFID tag undergoing the bending test sequence.

3. The RFID tag-bending test apparatus of claim 2, wherein the bending orientation-specific custom-shaped hook is designed for a vertical bending axis of the RFID tag, a horizontal bending axis of the RFID tag, or a diagonal bending axis of the RFID tag.

4. The RFID tag-bending test apparatus of claim 1, wherein the one or more tag holding clips are adjustable to accommodate various sizes of RFID tags.

5. The RFID tag-bending test apparatus of claim 1, wherein the bending axis rod assists transformation of the rotational force originating from the electrical motor into a cyclical bending force exerted on the RFID tag, wherein the cyclical bending force appears as the squeezing action of the one or more tag holding clips on the RFID tag.

6. The RFID tag-bending test apparatus of claim 1, wherein the control panel unit comprises a master stop button, a master start button, a main power on/off switch, a main power on/off indicator, and a tag-bending station control unit with an electrical motor on/off switch per station, a speed adjustment knob per station, and a bending test counter per station.

7. The RFID tag-bending test apparatus of claim 1, further comprising an RFID reader attached to or located near a casing of the RFID tag-bending test apparatus, wherein the RFID reader can perform test read/write operations to the RFID tag after a completion of the bending test sequence.

8. The RFID tag-bending test apparatus of claim 1, wherein the power supply unit is configured to operate with an external 220 Volt AC electrical outlet, and wherein the electrical motor is configured to consume up to 90 Watts of power at a maximum motor speed.

9. The RFID tag-bending test apparatus of claim 1, wherein the tag-bending station and the one or more tag holding clips can accommodate a plurality of RFID tags for the bending test sequence.

10. The RFID tag-bending test apparatus of claim 1, further comprising additional tag-bending stations operatively connected to additional electrical motors to increase bending test capacity of the RFID tag-bending test apparatus.

11. The RFID tag-bending test apparatus of claim 1, wherein the RFID tag is a battery-less or a battery-free passive tag, and wherein the RFID tag is designed to be used for livestock animal applications.

12. The RFID tag-bending test apparatus of claim 1, wherein the bending test sequence comprises a number of bending cycles or a number of bending test operations.

13. A method of testing an RFID tag with an external bending pressure simulation using an RFID tag-bending test apparatus, the method comprising the steps of:

securely placing one or more RFID tags in corresponding tag holding clips on the RFID tag-bending test apparatus;

configuring the RFID tag-bending test apparatus using a control panel unit to adjust a bending speed, a number of bending cycles, and a bending test sequence for the one or more RFID tags;

initiating the bending test sequence by activating an electrical motor of the RFID tag-bending test apparatus;

completing the bending test sequence for the one or more RFID tags based on a configured number of bending cycles by a user; and checking functionality of the one or more RFID tags by performing read or write operation to each of the one or more RFID tags, which completed the bending test sequence.

* * * * *